United States Patent
Cao

(10) Patent No.: US 10,297,346 B2
(45) Date of Patent: May 21, 2019

(54) APPOINTMENT-MAKING SERVER AND APPOINTMENT-MAKING METHOD

(71) Applicants: Fu Tai Hua Industry (Shenzhen) Co., Ltd., Shenzhen (CN); HON HAI PRECISION INDUSTRY CO., LTD., New Taipei (TW)

(72) Inventor: Dan Cao, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 993 days.

(21) Appl. No.: 14/789,262

(22) Filed: Jul. 1, 2015

(65) Prior Publication Data

US 2016/0063194 A1     Mar. 3, 2016

(30) Foreign Application Priority Data

Sep. 2, 2014   (CN) .......................... 2014 1 0442058

(51) Int. Cl.
*G16H 40/20*      (2018.01)
*G06F 19/00*      (2018.01)

(52) U.S. Cl.
CPC ............. *G16H 40/20* (2018.01); *G06F 19/00* (2013.01)

(58) Field of Classification Search
CPC ........ G06Q 50/22; G06Q 50/24; G06Q 10/10; G16H 10/60; G16H 40/20; G16H 80/00; G16H 50/70; G06F 19/3418; G06F 19/3481; G06F 19/328
See application file for complete search history.

(56) References Cited

U.S. PATENT DOCUMENTS

2009/0313076 A1* 12/2009 Schoenberg ......... G06Q 10/109
                                                               705/2
2013/0018672 A1*  1/2013 Wong .................... G06F 19/328
                                                               705/3

FOREIGN PATENT DOCUMENTS

CN      101957887 A      1/2011
TW      201340028 A     10/2013

* cited by examiner

Primary Examiner — Joseph D Burgess
(74) Attorney, Agent, or Firm — ScienBiziP, P.C.

(57) ABSTRACT

In an appointment-making method for a user's mobile device, a request for an appointment with a doctor is transmitted by the mobile device. Information as to doctors and services available for patient registration therewith is obtained and transmitted to the mobile device. A confirmation response from user's mobile device is received, and an appointment with a doctor is fixed. A registration number is assigned to the user in response to the received confirmation response. According to the assigned registration number, a patient queue for the doctor or the department is established, based on a predefined queue algorithm. Data as to queue length associated with the registration number is transmitted to the mobile device and payment of medical fees can also be made through the mobile device.

20 Claims, 4 Drawing Sheets

US 10,297,346 B2

APPOINTMENT-MAKING SERVER AND APPOINTMENT-MAKING METHOD

CROSS-REFERENCE TO RELATED APPLICATIONS

This application claims priority to Chinese Patent Application No. 201410442058.1 filed on Sep. 2, 2014, the contents of which are incorporated by reference herein.

FIELD

The subject matter herein generally relates to telecommunications technology.

BACKGROUND

When a patient goes to the hospital to see a doctor, the patient needs to queue for registration, to queue for being diagnosed by the doctor, to queue for paying fee, and to queue for medicine. A patient might make an appointment with a doctor by telephone or online at hospital website.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
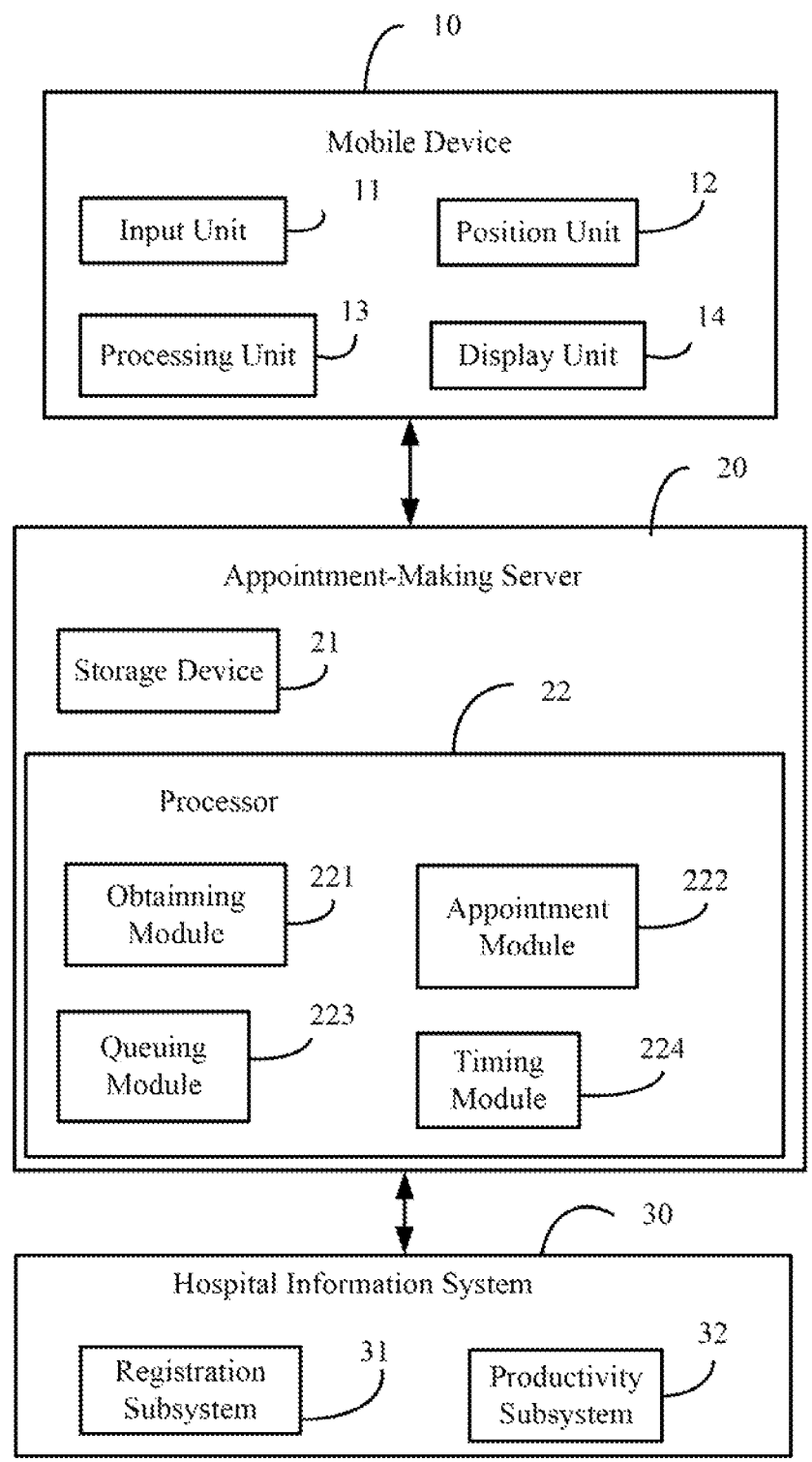
FIG. 1 is a block diagram of one embodiment of function modules of an appointment-making system.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts can be exaggerated to better illustrate details and features of the present disclosure.

Several definitions that apply throughout this disclosure will now be presented.

The present disclosure, including the accompanying drawings, is illustrated by way of examples and not by way of limitation. Several definitions that apply throughout this disclosure will now be presented. It should be noted that references to "an" or "one" embodiment in this disclosure are not necessarily to the same embodiment, and such references mean "at least one."

The word "module," as used hereinafter, refers to logic embodied in hardware or firmware, or to a collection of software instructions, written in a programming language, such as, for example, Java, C, or assembly. One or more software instructions in the modules may be embedded in firmware. It will be appreciated that modules may comprise connected logic units, such as gates and flip-flops, and may comprise programmable units, such as programmable gate arrays or processors. The modules described herein may be implemented as either software and/or hardware modules and may be stored in any type of non-transitory computer-readable storage medium or other computer storage device. The term "comprising," when utilized, means "including, but not necessarily limited to"; it specifically indicates open-ended inclusion or membership in the so-described combination, group, series and the like. The term "appointment" when used, means "obtaining a hospital clinical registration number associated with a particular doctor in order that a patient can be seen by the doctor with the registration number."

FIG. 1 is a block diagram of a first embodiment of function modules of a hospital or clinic appointment-making system (hereinafter "appointment-making system"). The appointment-making system includes a mobile device 10, an appointment-making server 20, and a hospital information system 30.

The appointment-making server 20 can obtain registration information from the hospital information system 30, and enable patients to make appointments with doctors via the mobile device 10. In the embodiment, the appointment-making server 20 is run and managed by a hospital or administrative department that employs the appointment-making system. The mobile device 10 is used by a patient. The mobile device 10 can be a tablet computer, a notebook computer, a smart phone, a personal digital assistant (PDA), or other suitable electronic device that has communication function.

The mobile device 10, the appointment-making server 20, and the hospital information system 30 each includes a communication module or a communication unit (not shown in the drawings). The mobile device 10 and the hospital information system 30 can communicate with the appointment-making server 20 via digital data network (DDN), WIFI, or the Internet.

The mobile device 10 includes an input unit 11, a position unit 12, a processing unit 13, and a display unit 14. The input unit 11 can input a request for a doctor's appointment in response to a first input operation of a patient. In one embodiment, the request carries information such as an identity of the patient and a clinical or department section the patient wants to visit. In another embodiment, the request further carries a name of a preferred doctor. In the embodiment, the identity of the patient is represented by telephone number of the mobile device 10. The position unit 12 can establish a current location of the mobile device 10. In the embodiment, the position unit 12 can be a global positioning system (GPS) unit. The processing unit 13 can determine whether the mobile device 10 is currently located in a predefined area, for example, in an area covered by a hospital that employs the appointment-making system. When the mobile device 10 is currently located in the predefined area, the processing unit 13 can generate an appointment-making request and send the appointment-making request to the appointment-making server 20.

The hospital information system 30 includes a registration subsystem 31 and a productivity subsystem 32. The registration subsystem 31 records current registration data of each clinical section or department of a hospital. In the embodiment, the registration data includes doctors of each clinical section who can diagnose patients and official working hours of each doctor. The productivity subsystem 32 records an average time spent by a doctor in making a patient diagnosis.

The appointment-making server 20 includes a storage device 21 and a processor 22. The processor 22 includes an obtaining module 221, an appointment module 222, a queuing module 223, and a timing module 224.

The storage device 21 can include various types of non-transitory computer-readable storage mediums. For example, the storage device 21 can be an internal storage system, such as a flash memory, a random access memory (RAM) for temporary storage of information, and/or a read-only memory (ROM) for permanent storage of information. The storage device 21 can also be an external storage system, such as a hard disk, a storage card, or a data storage medium. The processor 22 can be a central processing unit (CPU), a microprocessor, or other data processor chip that performs functions of the appointment-making server 20.

When the mobile device 10 transmits the request for an appointment with a doctor to the appointment-making server 20, the obtaining module 221 receives the request. The obtaining module 221 can obtain current registration data from the registration subsystem 31 of the hospital information system 30 and transmit the obtained registration data to the mobile device 10 in a predefined way, through the internet, for example, or via a short message or email. In the embodiment, the registration data carries registration numbers of the doctors currently available to patients.

In the embodiment, the obtaining module 221 obtains current registration data of all doctors in a clinical section specified in the request. In another embodiment, the obtaining module 221 obtains current registration data of a certain doctor which may be specified in the request.

The mobile device 10 receives the current registration data transmitted by the obtaining module 221, and displays the data on the display unit 14 of the mobile device 10. The processing unit 13 can generate a confirmation response to fix an appointment with a particular doctor, in response to a second operation applied on the input unit 11. Such second operation may be, for example, when a patient selects an available item displayed on the display unit 14. The processing unit 13 transmits the confirmation response, to fix an appointment with a particular doctor, to the appointment-making server 20.

The appointment module 222 receives the confirmation response transmitted by the processing unit 13 of the mobile device 10. The appointment module 222 can assign a registration number when the confirmation response is received. The registration number is associated with the particular doctor. The queuing module 223 can establish a length of a queue of patients who are to precede the assigned registration number according to a queue algorithm, generate queue data associated with the registration number, and transmit the queue data together with the registration number to the mobile device 10. In the embodiment, the queue data includes an order of the registration number and the number of prior patients listed in a patient queue.

The timing module 224 can obtain an average time which the doctor spends in making a patient diagnosis from the hospital information system 30, determine a likely patient waiting time according to the obtained average time and factor the number of prior patients listed in the patient queue, and transmit a relevant data to the mobile device 10. The relevant data includes the likely patient waiting time.

Figure 2:
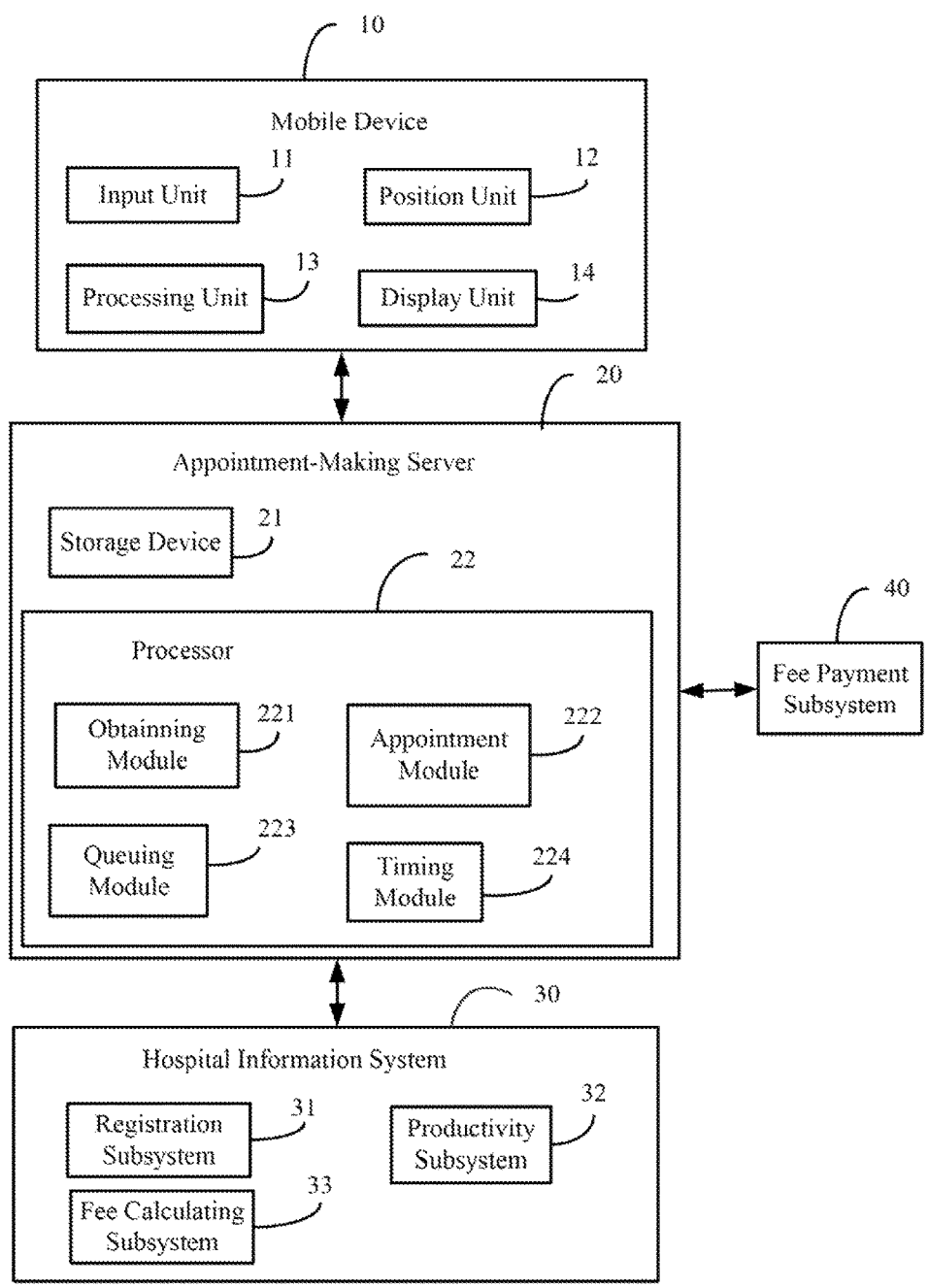
FIG. 2 is a block diagram of another embodiment of function modules of an appointment-making system.

FIG. 2 is a block diagram of a second embodiment of function modules of an appointment-making system. The appointment-making system further includes a fee payment subsystem 40. The mobile device 10 and the appointment-making server 20 can communicate with the fee payment subsystem 40.

The hospital information system 30 further includes a fee calculating subsystem 33. The fee calculating subsystem 33 records diagnostic fees associated with each registration number. The appointment module 222 further obtains a diagnostic fee associated with a registration number from the hospital information system 30 and transmits the obtained diagnostic fee to the mobile device 10. A patient can pay the diagnostic fee through the fee payment subsystem 40. The fee payment subsystem 40 can be an online bank, a social security center, or a third-party payment platform such as Alipay.

After a patient pays the diagnostic fee through the fee payment subsystem 40, the fee payment subsystem 40 sends a notice to the appointment-making server 20. The queuing module 223 of the appointment-making server 20 accordingly analyses the patient queue relevant to the registration number.

Figure 3:
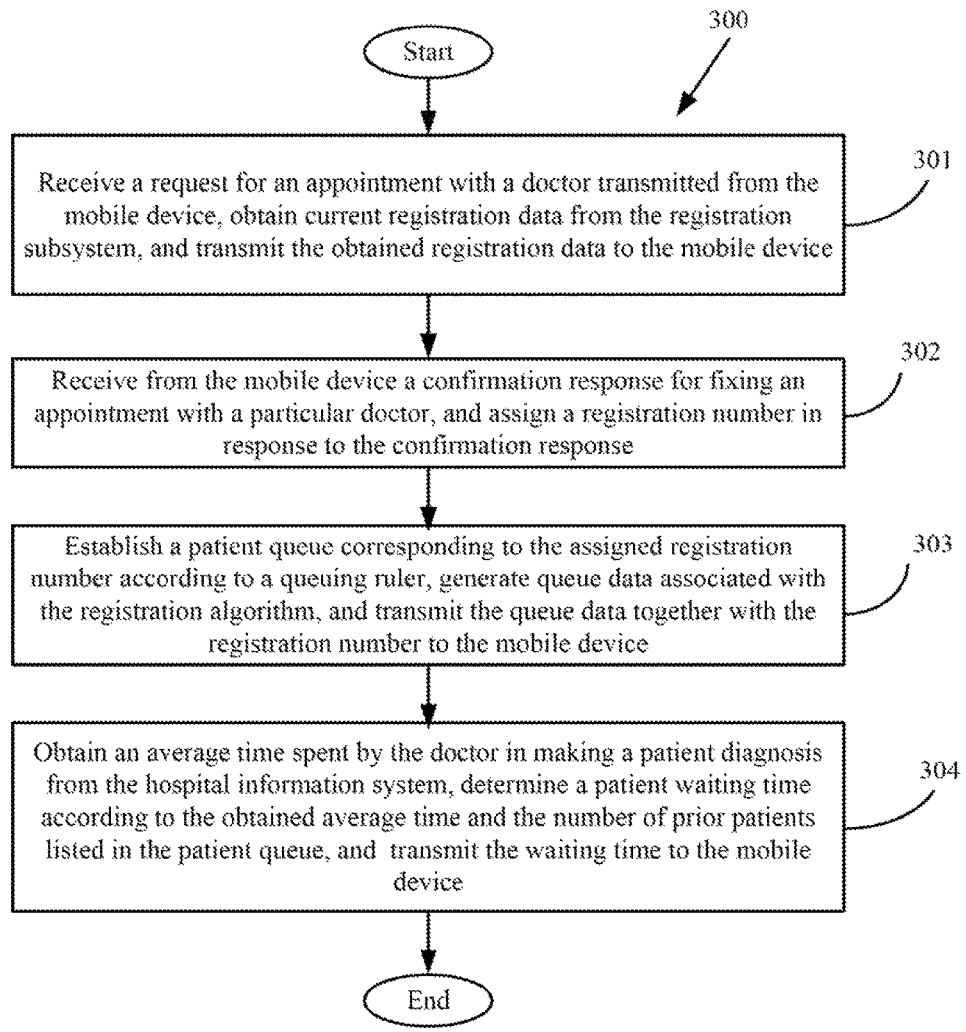
FIG. 3 is a flowchart of one embodiment of an appointment-making method.

FIG. 3 is a flowchart of one embodiment of an appointment-making method. The example method 300 is provided by way of example, as there are a variety of ways to carry out the method. The method 300 described below can be carried out using the configurations illustrated in FIGS. 1 and 3, for example, and various elements of these figures are referenced in explaining example method 300. Each block shown in FIG. 3 represents one or more processes, methods, or subroutines, carried out in the exemplary method 300. Additionally, the illustrated order of blocks is by example only and the order of the blocks can change. The exemplary method 300 can begin at block 301. Depending on the embodiment, additional steps can be added, others removed, and the ordering of the steps can be changed.

At block 301, the obtaining module receives a request for a doctor's appointment transmitted from the mobile device, obtains current registration data from the registration subsystem, and transmits the obtained registration data to the mobile device.

At block 302, the appointment module receives from the mobile device a confirmation response for fixing an appointment with a particular doctor, and assigns a registration number in response to the confirmation response.

At block 303, the queuing module establishes a patient queue corresponding to the assigned registration number according to a queue algorithm, generates queue data associated with the registration number, and transmits the queue data together with the registration number to the mobile device.

At block 304, the timing module obtains an average time spent by the doctor in making a patient diagnosis from the hospital information system, determines a patient waiting time according to the obtained average time and the number of prior patients listed in the patient queue, and further transmits the waiting time to the mobile device.

Figure 4:
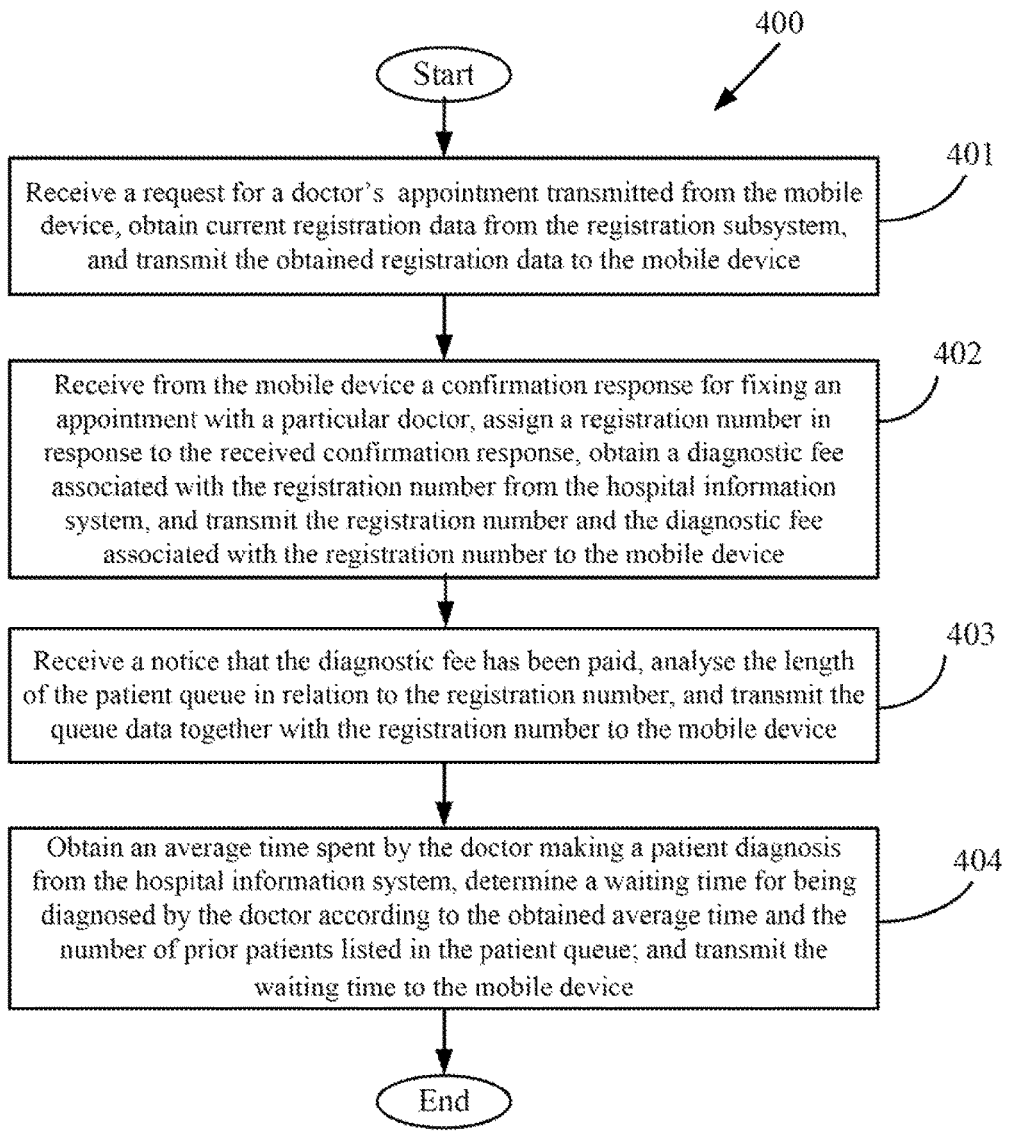
FIG. 4 is a flowchart of another embodiment of an appointment-making method.

FIG. 4 is a flowchart of another embodiment of an appointment-making method. The example method 400 is provided by way of example, as there are a variety of ways to carry out the method. The method 400 described below can be carried out using the configurations illustrated in FIGS. 2 and 4, for example, and various elements of these figures are referenced in explaining example method 400. Each block shown in FIG. 4 represents one or more processes, methods, or subroutines, carried out in the exemplary method 400. Additionally, the illustrated order of blocks is by example only and the order of the blocks can change. The exemplary method 400 can begin at block 401. Depending on the embodiment, additional steps can be added, others removed, and the ordering of the steps can be changed.

At block 401, the obtaining module receives a request for a doctor's appointment transmitted from the mobile device, obtains current registration data from the registration subsystem, and transmits the obtained registration data to the mobile device.

At block 402, the appointment module receives from the mobile device a confirmation response for fixing an appointment with a particular doctor, assigns a registration number in response to the received confirmation response, obtains a diagnostic fee associated with the registration number from the hospital information system, and transmits the registration number and the diagnostic fee associated with the registration number to the mobile device.

At block 403, the queuing module receives a notice that the diagnostic fee has been paid, analyses the length of the patient queue in relation to the registration number, and transmits the queue data together with the registration number to the mobile device.

At block 404, the timing module obtains an average time spent by the doctor making a patient diagnosis from the hospital information system, determines a waiting time for being diagnosed by the doctor according to the obtained average time and the number of prior patients listed in the patient queue; and transmits the waiting time to the mobile device.

The embodiments shown and described above are only examples. Many details are often found in the art and many such details are therefore neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. An appointment-making method for a user's mobile device executable by a processor of a computing device, the computing device communicating with a mobile device and a hospital information system, the method comprising:
   receiving a request for an appointment with a doctor transmitted by the mobile device;
   obtaining current registration data from the hospital information system, the registration data carrying registration numbers of the doctors currently available to patients;
   transmitting the obtained registration data to the mobile device;
   receiving a confirmation response from the mobile device for fixing an appointment with a particular doctor;
   assigning a registration number when the confirmation response is received, the registration number associated with the particular doctor;
   establishing a patient queue corresponding to the assigned registration number according to a predefined queue algorithm;
   generating queue data associated with the registration number; and
   transmitting the queue data together with the registration number to the mobile device.

2. The method according to claim 1, further comprising:
   obtaining an average time spent by the particular doctor in making a patient diagnosis from the hospital information system;
   determining a waiting time that a user of the mobile device needs to wait for being diagnosed by the doctor according to the obtained average time and the number of prior patients listed in the queue data; and
   transmitting the waiting time to the mobile device.

3. The method according to claim 2, wherein the request comprises an identity of a patient, a clinical or a department section, and a doctor that the patient wants to visit.

4. The method according to claim 3, wherein the registration data carries registration numbers of all doctors in a clinical or a department section specified in the request.

5. The method according to claim 3, wherein the registration data carries registration numbers of the particular doctor specified in the request.

6. The method according to claim 1, further comprising:
   obtaining diagnostic fee associated with the registration number from the hospital information system, and
   transmitting the obtained diagnostic fee to the mobile device.

7. The method according to claim 6, wherein the patient queue on the registration number is analyzed after a notice that the patient pays the diagnostic fee is received from the mobile device.

8. An appointment-making server, making communication with a mobile device and a hospital information system, comprising:
   a processor; and
   a storage device coupled to the processor, the storage device stores one or more programs which, when executed by the processor, cause the processor to:
   receive a request for an appointment with a doctor transmitted by the mobile device;
   obtain current registration data from the hospital information system, the registration data carrying registration numbers of the doctors currently available to patients;
   transmit the obtained registration data to the mobile device;
   receive a confirmation response from the mobile device for fixing an appointment with a particular doctor;
   assign a registration number when the confirmation response is received, the registration number associated with the particular doctor;
   establish a patient queue corresponding to the assigned registration number according to a predefined queue algorithm;
   generate queue data associated with the registration number; and
   transmit the queue data together with the registration number to the mobile device.

9. The appointment-making server according to claim 8, wherein the processor is further caused to:
   obtain an average time spent by the particular doctor in making a patient diagnosis from the hospital information system;

determine a waiting time that a user of the mobile device needs to wait for being diagnosed by the doctor according to the obtained average time and the number of prior patients listed in the queue data; and transmit the waiting time to the mobile device.

10. The appointment-making server according to claim 9, wherein the registration data carries registration numbers of all doctors in a clinical or a department section specified in the request.

11. The appointment-making server according to claim 9, wherein the registration data carries registration numbers of the particular doctor specified in the request.

12. The appointment-making server according to claim 8, wherein the processor is caused to:

obtain diagnostic fee associated with the registration number from the hospital information system, and transmitting the obtained diagnostic fee to the mobile device.

13. The appointment-making server according to claim 12, wherein the clinic queue on the registration number is conducted after a command that the patient paid for diagnostic expense is received from the mobile device.

14. A non-transitory storage medium having stored thereon instructions that, when executed by a processor of a computing device, causes the processor to perform an appointment-making method, wherein the method comprises:

receiving a request for an appointment with a doctor transmitted by an electronic device;

obtaining current registration data from a hospital information system, the registration data carrying registration numbers of the doctors currently available to patients;

transmitting the obtained registration data to the mobile device;

receiving a confirmation response from the mobile device for fixing an appointment with a particular doctor;

assigning a registration number when the confirmation response is received, the registration number associated with the particular doctor;

establishing a patient queue corresponding to the assigned registration number according to a predefined queue algorithm;

generating queue data associated with the registration number; and transmitting the queue data together with the registration number to the mobile device.

15. The non-transitory storage medium according to claim 14, further comprising:

obtaining an average time spent by the particular doctor in making a patient diagnosis from the hospital information system;

determining a waiting time that a user of the mobile device needs to wait for being diagnosed by the doctor according to the obtained average time and the number of prior patients listed in the queue data; and transmitting the waiting time to the mobile device.

16. The non-transitory storage medium according to claim 15, wherein the request comprises an identity of a patient, a clinic section, and a doctor that the patient wants to visit.

17. The non-transitory storage medium according to claim 16, wherein the registration data carries registration numbers of all doctors in a clinical or a department section specified in the request.

18. The non-transitory storage medium according to claim 16, wherein the registration data carries registration numbers of the particular doctor specified in the request.

19. The non-transitory storage medium according to claim 14, further comprising:

obtaining diagnostic fee associated with the registration number from the hospital information system, and transmitting the obtained diagnostic fee to the mobile device.

20. The non-transitory storage medium according to claim 19, wherein the patient queue on the registration number is analyzed after a notice that the patient pays the diagnostic fee is received from the mobile device.

* * * * *